United States Patent [19]
Siegel et al.

[11] Patent Number: 5,695,460
[45] Date of Patent: *Dec. 9, 1997

[54] ENHANCEMENT OF ULTRASOUND THROMBOLYSIS

[75] Inventors: Robert J. Siegel, Venice, Calif.; Robert E. Carter, Arlington, Mass.

[73] Assignee: Coraje, Inc., San Francisco, Calif.

[*] Notice: The term of this patent shall not extend beyond the expiration date of Pat. No. 5,509,896.

[21] Appl. No.: 441,127

[22] Filed: May 15, 1995

Related U.S. Application Data

[63] Continuation-in-part of Ser. No. 303,858, Sep. 9, 1994, Pat. No. 5,509,896.
[51] Int. Cl.⁶ ..................................................... A61N 1/30
[52] U.S. Cl. .................. 604/21; 604/52; 604/22; 128/660.01; 601/3
[58] Field of Search .................. 604/19–22, 49, 604/52, 53; 128/653.4, 660.2, 660.01; 601/2–3

[56] References Cited

U.S. PATENT DOCUMENTS

| | | | |
|---|---|---|---|
| 4,586,512 | 5/1986 | Do-huu | 128/660 |
| 4,620,546 | 11/1986 | Aida | 128/660 |
| 4,622,952 | 11/1986 | Gordon | 604/20 X |
| 4,658,828 | 4/1987 | Dory | 128/660 |
| 4,718,433 | 1/1988 | Feinstein | 128/660.02 X |
| 4,900,540 | 2/1990 | Ryan et al. | 424/9 |
| 5,149,319 | 9/1992 | Unger | 604/22 |
| 5,196,183 | 3/1993 | Yudelson | 128/660.02 X |
| 5,197,946 | 3/1993 | Tachibana | 604/22 |
| 5,215,680 | 6/1993 | D'Arrigo | 128/660.02 X |
| 5,230,882 | 7/1993 | Unger | 128/660.02 X |
| 5,352,435 | 10/1994 | Unger | 128/660.02 X |
| 5,380,411 | 1/1995 | Schlief | 204/157.15 |
| 5,399,158 | 3/1995 | Lauer | 604/22 |
| 5,405,318 | 4/1995 | Nita | 604/22 |
| 5,487,390 | 1/1996 | Cohen | 128/660.02 |
| 5,509,896 | 4/1996 | Carter | 604/21 |

Primary Examiner—Mark Bockelman
Assistant Examiner—Chalin Smith
Attorney, Agent, or Firm—Walter A. Hackler

[57] ABSTRACT

Apparatus and methods are provided for utilizing a combination of ultrasonic energy and an echo contrast agent containing microbubbles, for substantially dissolving blood clots or other vascular obstructions. One embodiment of the present invention utilizes a selected dose of thrombolytic agent in combination with an echo contrast agent, for enhancing the thrombolytic action of a thrombolytic agent and removing a thrombosis from a vascular system in less time than the time required by activity of the selected dose of thrombolytic agent without the ultrasonic radiation of the thrombosis.

19 Claims, 1 Drawing Sheet

ENHANCEMENT OF ULTRASOUND THROMBOLYSIS

This application is a continuation-in-part of U.S. patent application Ser. No. 08/303,858, filed Sep. 9, 1994 now U.S. Pat. No. 5,509,896.

The present invention is generally related to the use of ultrasonic energy and is more particularly directed to the use of ultrasound with ultrasound imaging agents, alone or in combination with thrombolytic agents, to dissolve arterial thrombi.

It is known that ultrasound imaging can be used to locate intravascular thrombi and it has been demonstrated that the utilization of ultrasonic waves can improve the diffusion and penetration of medicinal fluids or the like into the vascular system (see U.S. Pat. No. 5,197,946 to Tachibana). Tachibana teaches that in order to effectively enhance or improve the diffusion and penetration of a medicinal fluid, the oscillating element must be disposed at the point of injection of the medicinal fluid.

This is to be contrasted, according to Tachibana, with prior art techniques which utilize ultrasonic waves and a catheter wire for diffusion and penetration of medicinal fluids. In this arrangement the ultrasonic oscillating element is connected to the catheter wire outside the body and far from a radiating end of the catheter wire. This results in a significant reduction in efficient coupling of the ultrasound due to the damping of ultrasonic energy in the course of transmission down the catheter wire.

Other disadvantages in the use of a transmission wire to deliver ultrasonic energy to a thrombosis is transmission wire stiffness. Further, as the transmission wire diameter is reduced to lower the stiffness thereof, it is more difficult to deliver sufficient energy for effective removal of the thrombosis. To overcome these disadvantages, miniature ultrasonic ablation tools have been developed, utilizing ultrasonic transducers sized for arterial insertion. While these devices overcome the transmission wire difficulties, their small size severely limits the amount of ultrasonic energy available for direct mechanical action for fragmenting plaque and thrombosis and/or energy for improving diffusion and penetration of medicinal fluids as described in U.S. Pat. No. 5,197,946.

Ultrasonic apparatus have also been utilized to assist in the delivery of medicaments in specific areas of a vein. For example, U.S. Pat. No. 5,040,537 to Katakura teaches the use of injecting numerous fine capsules, with an agent being packed therein, into a patient's body and thereafter applying a shock wave to provide dominant positive pressure from outside the body to rupture the capsules dispersed in the body.

Thus, ultrasonic energy in the form of a pulsated shock wave is generated exterior to the body and imaged to selectively burst agent-containing capsules in order to selectively release the agent into the blood.

The present invention is directed to the discovery that ultrasound diagnostic media, particularly echo contrast agents containing microbubbles, utilized in conjunction with ultrasound, provides a safe and effective method for dissolving arterial thrombi without the use of thrombolytic drugs. Notably, the ultrasound may be transcutaneously applied, applied by means of a transmission wire or generated intravascularly by means of a miniature ultrasonic tool. Moreover, a method in accordance with the present invention has been found to substantially enhance prior art treatments of thrombosis.

SUMMARY OF THE INVENTION

A method in accordance with the present invention utilizes the discovery of the effectiveness of applying a combination of ultrasonic energy and certain agents, including ultrasound imaging agents, to dissolve arterial thrombi. Particularly, the present invention includes a method for substantially reducing and removing a thrombosis disposed within a body vessel by radiating an ultrasound imaging agent, particularly a microbubble containing echo contrast agent, proximate the thrombosis vessel, with ultrasound. The ultrasound may be applied intravascularly, by means of a miniature ultrasonic transducer, or by a guide wire for transmitting ultrasound directly into the vessel, or transcutaneously by means of an external generator and transducer. Importantly, the introduction of a thrombolytic agent proximate the thrombosis further enhances the clot dissolution capability of a method in accordance with the present invention. This step is carried out during thrombolytic action by the thrombolytic agent on the thrombosis disposed within the body vessel.

This method is clearly distinguished from prior art techniques such as taught by Katakura in U.S. Pat. No. 5,040,537, in which ultrasound generated exterior to the body vessel is used only to rupture capsules containing an active agent. Clearly, the prior art is specifically directed to the release of an active agent within a vessel, whereas the present invention is directed to introduction of a microbubble media that does not contain an active agent, in order to enhance the effect of ultrasound in removal of thrombosis and increase the effect of a thrombolytic agent during its activity in dissolving, or splitting up, a thrombus. The present invention involves a phenomena of long and short range ultrasound enhancement of inherent drug activity.

In accordance with one embodiment of the present invention, a selected dose of an echo contrast agent is injected into an occluded vessel, and ultrasonic energy is radiated from an external source into the echo contrast agent transcutaneously. It has been found that at certain frequencies of ultrasonic radiation, the thrombosis is substantially dissolved using this combination of steps. This embodiment of the present invention is based on the discovery that the use of echo contrast agents, particularly microbubble media, substantially increases the effectiveness of ultrasound therapy in removing cardiovascular blockages.

By way of specific example only, the echo contrast agent may be dodecafluropentane colloid dispersion, and the ultrasound may be introduced at a frequency of between about 24 kHz and about 53 kHz.

Thus, one embodiment of the preset invention includes the step of introducing an echo contrast agent alone, proximate the thrombosis, and subsequently directing ultrasound into the thrombosis and proximate echo contrast agent, in order to substantially dissolve the thrombosis without the use of thrombolytic agents. The echo contrast agent may one of several presently available types containing microbubbles and currently marketed for ultrasound diagnostic purposes, such as dodecafluropentane (under trademark "Echogen"), and sonicated albumin (under trademark "Albumex").

Another embodiment of the present invention comprises the use of a miniature ultrasound transducer inserted intravascularly proximate the thrombosis, such as the transducer disclosed in U.S. Pat. No. 5,269,291, said being incorporated herein in toto by this specific reference thereto. Thus, a method in accordance with this particular embodiment comprises introducing an echo contrast agent proximate the thrombosis and subsequently radiating the thrombosis and surrounding vessel with ultrasound transmitted internally from a miniature ultrasound transducer tip.

It should be appreciated that another workable method of transmitting ultrasound is by means of a catheter, or guide wire, inserted intravascularly to a position proximate the thrombosis, in order to transmit ultrasound along the wire from an external source.

The present invention also encompasses the enhancement, or acceleration, of the activity of an thrombolytic agent, and in that regard includes the steps of introducing a selected dose of an echo contrast agent and thrombolytic agent, proximate to a thrombosis disposed in the vessel of a body and radiating the thrombosis with ultrasound in order to effect removal of the thrombosis in less time than required by activity of the selected dose of thrombolytic agent without ultrasound radiation of the thrombosis.

In other words, the present invention for enhancing thrombolytic action of a thrombolytic agent includes the steps of injecting a combination of echo contrast agent and thrombolytic agent or disruptive agent, proximate a thrombosis disposed in a vessel within a body, and providing transcutaneous or intravascular application of ultrasound proximate the thrombosis, with sufficient energy to increase the thrombolytic action of the thrombolytic agent.

The present invention therefore also encompasses a method for removing a cardiovascular obstruction and in that regard includes the steps of delivering an echo contrast agent, alone or in combination with a thrombolytic agent, proximate a cardiovascular obstruction disposed in a vessel within a body and directing ultrasound at the cardiovascular obstruction with proximate agents, of sufficient energy to remove the cardiovascular obstruction from the vessel.

More particularly, in accordance with the present invention, the thrombolytic agent introduced may be any agent having suitable activity, such as, for example, streptokinase, staphlokinase, urokinase or a tissue plasminogen activator (TPA). These agents are set forth herein only by way of example and it should be appreciated that, as hereinabove recited, any thrombolytic agent has possible use in accordance with the present invention.

Additionally, the radiation by ultrasound may include continuous or pulsed radiation. Still more particularly, by way of specific example only, the amount of streptokinase introduced may be in concentrations of less than about 2,000 µ/ml.

In conjunction with the hereinabove enumerated method defining the present invention, also encompassed is an apparatus for the removal of a cardiovascular blockage which, in combination, includes ultrasonic means for radiating a cardiovascular blockage disposed within a body vessel and means for introducing a selected dose of an echo contrast agent proximate the cardiovascular blockage in order to enhance the effect of the ultrasound in removing the cardiovascular blockage.

Clearly, the prior art teaches away from this discovery since prior art workers only were able to obtain enhancement for release of thrombolytic drugs within a vessel by introduction of ultrasound alone, which was thought to be due to mechanical agitation of surrounding vessel walls, as pointed out by Tachibana in U.S. Pat. No. 5,197,946. It must be accepted that the mechanism taught by the Tachibana reference is not applicable to the present discovery in which it has been found that the introduction of an echo contrast agent proximate thrombosis, and subsequent ultrasonic radiation of the agent and thrombosis, substantially dissolves thrombi, with or without the use of thrombolytic agents.

BRIEF DESCRIPTION OF THE DRAWINGS

The advantages and features of the present invention will be better understood by the following description when considered in conjunction with the accompanying drawings in which.

DETAILED DESCRIPTION

Figure 1:
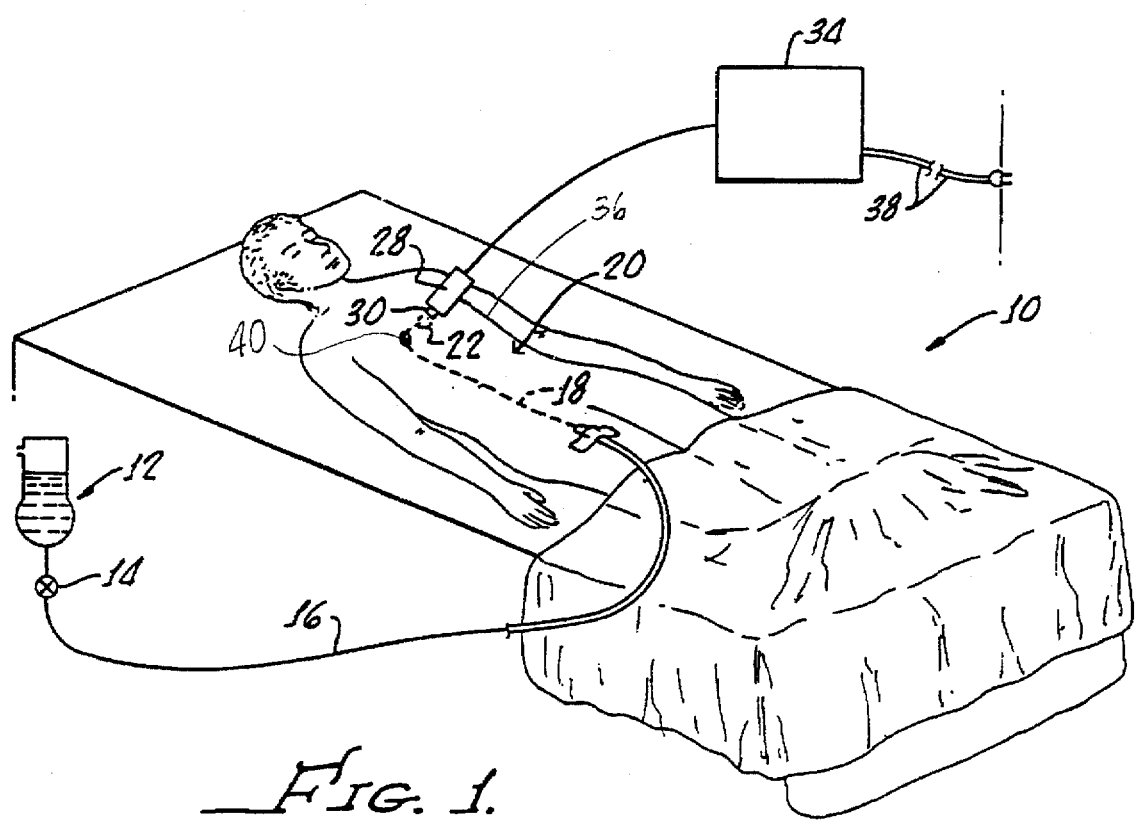
FIG. 1 is a diagram of ultrasonic surgical apparatus in accordance with the present invention or teaching method for removing a thrombosis, as well as enhancing the thrombolytic action of a thrombolytic agent.

Turning now to FIG. 1, there is shown apparatus 10 in accordance with the present invention for both enhancing the effectiveness of ultrasound in removing a thrombosis and for enhancing thrombolytic action of a thrombolytic agent which may include a vial 12 of a selected dose of an echo contrast agent alone or in combination with a thrombolytic agent which, by way of a valve 14 and a catheter 16, provides a means for injecting, introducing and delivering the agents, to a vessel 18 within a body 20, proximate a thrombosis 22 illustrated by the dashed lines in FIG. 1.

Alternatively, the agents can be introduced or injected into the vessel 18 proximate the thrombosis 22 in any conventional manner, including, for example, hypodermic needle or the like (not shown).

Also shown in FIG. 1 is a transducer 28 having a tip 30 positioned exterior to the body 12 and interconnected to an oscillator/driver 34 which provides means for radiating the cardiovascular blockage 22 with ultrasound in order to effect removal thereof. In this embodiment of the present invention, the ultrasound is transmitted transcutaneously and thus the step of radiating ultrasound is a "non-invasive" procedure.

The ultrasonic transducer 28 may be of any conventional design with a frequency range of about 19 kHz to about 1 MHz, the frequency being manually adjustable for transmitting ultrasonic frequency through the tip 30. The frequency range may be limited to a range of between about 20 kHz and about 500 kHz if desired.

The tip 30 provides means for coupling the ultrasound through a body surface 36, thus enabling transcutaneous, or transdermal, application of the ultrasound. It should be appreciated that the tip 30 can include means for focusing the ultrasound as may be required in order to concentrate or specifically direct the ultrasound to a desired area or volume.

The driver 34 is powered through conventional 110 volt line 38 and may have a power output of up to, for example, about 50 watts through a tip active area of about 0.75 inches by 0.75 inches. The power levels obtainable from the ultrasonic transducer 28 are capable of producing violent cavitation in tap water at atmospheric pressure and the limiting factor of introducing ultrasonic power into the body 20 would be possible skin irritation despite the output capability of the device. The driver 34 and transducer may be operated at a duty cycle of 100%, i.e., continuous output, or pulse-operated at, for example, a 50% duty cycle.

Alternately, ultrasound may be transmitted intravascularly, rather than transcutaneously as hereinabove described. For example, a miniature ultrasonic transducer 40, such as the device described in U.S. Pat. No. 5,269,291, incorporated herein by reference, may be utilized as a means for transmitting ultrasonic energy directly into and proximate the thrombosis 22 and surrounding vascular fluid. The miniature ultrasonic transducer 40 may be inserted by into the vessel 18 means of catheter 16.

It should be appreciated that ultrasound may be generated from driver 34 and transmitted therefrom via a guide wire (not shown) directly into the vessel 18, as is well known in the art.

In accordance with one embodiment of the present invention, the apparatus 10 is useful in the method of the present invention for removing a thrombosis, in which a selected dose of thrombolytic agent is introduced proximate the thrombosis 22 disposed within a vessel 18 in the body 20. The thrombosis 22 is radiated with ultrasound generated exterior to the body 20, or intravascularly as described above, to effect removal of the thrombosis 22 in less time than required by activity of the selected dose of thrombolytic agent without the ultrasound radiation of the thrombosis. Specific examples of this method will be shown in the examples following.

Another embodiment of the present invention includes introduction an echo contrast agent alone, by means of the vial 12 or other conventional manner, into the vessel 18 at a position proximate the thrombosis 22, and subsequently radiating ultrasound into the thrombosis 22. It has been found that the introduction of an echo contrast agent, in combination with the ultrasonic energy radiated into to the site of the thrombosis, will substantially increase the effectiveness of ultrasound in removing the thrombosis. This embodiment provides for substantial dissolution of the thrombosis without the need for the introduction of thrombolytic agents.

Importantly, it has been found that when ultrasound is applied at a lower, rather than a higher frequency, the effectiveness of the method is markedly enhanced. More particularly, when ultrasound is applied at less than about 100 kHz, and even more particularly, between approximately 25 kHz and approximately 53 kHz, the dissolution of thrombi is most significant. For example, at the frequency of about 53 kHz, the synergistic effect of a combination of ultrasound and echo contrast agent was most evident when compared to utilizing ultrasound alone.

More particularly, the echo contrast agent may be one of several types of microbubble media presently utilized for diagnostic ultrasound. Echo contrast agents can generally be classified into five groups: free gas bubbles, stabilized gas bubbles, colloidal suspensions, emulsions, and aqueous solutions. The aqueous solutions include aqueous solutions of air-filled proteinaceous microbubbles. Currently available products include gas filled liposomes, gas filled lipid bilayers, microbubbles containing liquids, gas emulsions, gas-filled microspheres and microbubbles containing suspensions.

Preferably, the echo contrast agent comprises dodecafluoropentane, a colloidal suspension, for example the agent presently marketed under the trademark "Echogen". Alternatively, sonicated human serum albumin, an aqueous solution, may be introduced as the echo contrast agent.

It is important to recognize that control experiments, which tested the effect on blood clots of an echo contrast agent, without ultrasound, have shown an absence of significant clot dissolution. It has also been found that high intensity, low frequency ultrasound does have an effect on clot dissolution. Importantly, a method in accordance with the present invention utilizes the surprising discovery that a combination of echo contrast agent and ultrasound, provides for effectively reducing or removing a thrombosis in less time than required by ultrasound radiation of the thrombosis without the use of said echo contrast agent. This may be due to the effect of microbubbles within the echo contrast agent that, when combined with ultrasonic energy, leads to increased cavitation of vascular fluid surrounding the thrombosis.

Another embodiment of the present invention includes the introduction of an echo contrast agent into the vessel 18 proximate the thrombosis 22, in order to increase the effectiveness of both a thrombolytic agent and ultrasound in removing the thrombosis. Preferably, the method includes the introduction of streptokinase as a thrombolytic agent into the vessel 18. As will be specifically set forth in the examples, the ultrasound may be continuously introduced or introduced in pulses, whereas the streptokinase may be introduced at concentrations of less than about 2,000 μl/ml.

In some instances, the method of the present invention not only provides enhancement, or acceleration, of the activity of the thrombolytic agent but also provides for removal of a thrombosis, utilizing a combination of ultrasound, echo contrast agent and thrombolytic agent, which otherwise cannot be removed through the use of a thrombolytic agent by itself. This is specifically set forth hereinafter in the following examples.

EXAMPLE I

Experimental Setup

Ultrasound device, Piezo driver, Model CU51-E-001, was produced by PIEZO Systems, Inc., Cambridge, Mass. The frequency of the machine is about 26 kHz. The transducer's overall dimensions are 6.5 cm in length and 2.0 cm in diameter. The output of ultrasound energy can be adjusted by turning both the amplitude knob and frequency knob. The output of ultrasound energy can be measured by watching the Power Meter (unit: microamperes). There are no direct meters to reflect the operating frequency and operating ultrasound intensity.

Results

About 200 clots from a health subject were used in serial in vitro studies to confirm that external ultrasound can enhance the thrombolytic action of a thrombolytic agent such as streptokinase. The results are as follows:

Clot reduction is dependent on the dosage of streptokinase. The effects of three different concentrations of streptokinase (SK) (50 μ/ml, 250 μ/l, 2,000 μ/ml) and ultrasound on one-hour old clot lysis were analyzed for thirty minutes. The results are shown in Table 1 for an ultrasound device at a power level of about 20 microamperes (pulsed mode), 40 microamperes (continuous mode), and in Table 2 for streptokinase alone.

It can be seen by comparison of Tables 1 and 2 that for a given dose of streptokinase, a significantly greater reduction in clot size (by weight percent) occurs when the clot is radiated with ultrasound for an equal period of time, 30 minutes. Therefore, a shorter length of time is required for a desired clot reduction when both ultrasound and the streptokinase are utilized as opposed to streptokinase itself.

TABLE 1

|  | USD + SK (50 μ/ml) | USD + SK (250 μ/ml) | USD + SK (2000 μ/ml) |
|---|---|---|---|
| reduction, % | 63% | 81% | 85% |
| weight reduction | 170 mg | 262 mg | 315 mg |

TABLE 2

|  | SK (50 µ/ml) | SK (250 µ/ml) | SK (2000 µ/ml) |
|---|---|---|---|
| reduction, % | 26% (n = 2) | 29 ± 6% (n = 7) | 48% (n = 2) |
| weight reduction | 48 ± 4 mg | 74 ± 24 mg | 130 ± 28 mg |

EXAMPLE II

Experimental Setup

In order to compare the thrombolytic properties of ultrasound with streptokinase and assess for a synergistic effect, four to six hour old human blood clots of average weight 265 mg, were exposed to 3 minutes of catheter delivered ultrasound alone, streptokinase alone, in different concentrations (50 U/l, 250 U/l, 2000 U/l), or the combination of both ultrasound and streptokinase at 2000 U/l.

Results

Streptokinase at 50 U/l reduced the thrombus weight from 225±12 mg to 202±12 mg, streptokinase at 250 U/l reduced the thrombus from 229±21 mg to 200±13 mg, and streptokinase at 2000 U/l reduced the weight from 250 mg ±7 mg to 210±10 mg.

Ultrasound alone reduced the thrombus weight from 239±9 mg to 23±4 mg. The combination of ultrasound and streptokinase reduced the thrombus weight from 263±7 mg to 11±2 mg. Over 99% of debris were less than 10 µm in size.

It was concluded that 1) ultrasound thrombus dissolution is more effective than streptokinase in vitro, 2) ultrasound and moderate doses of streptokinase may be synergistic in vitro, and 3) ultrasound could be clinically used as an alternative or to enhance standard thrombolysis.

EXAMPLE III

Experimental Setup

The effect of ultrasonic energy on clot dissolution was studied in order to determine the optimal ranges of ultrasound frequency for clot dissolution.

Several different ultrasound frequencies, more specifically 25, 29, 53, 66, 85, 105, and 243 kHz, at the power output of 50 watts, were tested on 56 human blood clots one to three hours old and weighing 240-300 mg each. Each clot was incubated in warm saline (37-42 degrees C.) and exposed to ultrasonic energy for three minutes. Eight clots were tested at each frequency.

Results

After three minutes of ultrasound exposure, the percent of dissolved clot was 99±1% at 25 kHz, 86±7% at 39 kHz, 45±15% at 53 kHz, 44±12% at 66 kHz, 36±4% at 85 kHz, 27±7% at 105 kHz, and 26±6% at 243 kHz.

Thus, it was concluded that clot dissolution is significantly greater with lower frequencies, between about 25 to about 39 kHz, compared to higher frequencies of ultrasound radiation. Thus, the use of lower frequencies of ultrasound radiation has potential as a primary or adjunctive therapy for thrombolysis.

EXAMPLE IV

Utilizing the sample experimental setup as in Example I, the function of clot reduction on ultrasound exposure time has been determined. With the combination of streptokinase (250 µ/ml) and ultrasound, one-hour old clot lysis were tested, using four different exposure times, 5 minutes, 10 minutes, 13 minutes and 30 minutes. The results are shown in Table 3.

TABLE 3

|  | Clot reduction rate | Clot weight reduction |
|---|---|---|
| 5 minutes subgroup (n = 1) | 30% | 30 mg |
| 10 minutes subgroup (n = 2) | 36 ± 16% | 36 ± 9 mg |
| 15 minutes subgroup (n = 8) | 46 ± 7% | 126 ± 33 mg |
| 30 minutes subgroup (n = 8) | 68 ± 9% | 211 ± 33 mg |

EXAMPLE V

Utilizing the same experimental setup as in Example I, the function of clot reduction on clot age has been determined, with 250 µ/ml streptokinase, combined with ultrasound for 30 minutes. The effect of clot age on thrombolysis is shown in Table 4.

TABLE 4

|  | Clot reduction % | Clot weight reduction |
|---|---|---|
| 1-hour old clot (n = 6) | 74 ± %9% | 217 ± 35 mg |
| 2-hour old clot (n = 5) | 68 ± 9% | 204 ± 27 mg |
| 3-hour old clot (n = 2) | 67 ± 4% | 184 ± 14 mg |

EXAMPLE VI

Utilizing the same experimental setup as in Example I, the function of thrombolysis on different clot weights has been determined with 250 µ/ml streptokinase, combined with ultrasound for 30 minutes. The effects of 1-hour old clot weight and mass on thrombolysis is shown in Tables 5 and 6.

TABLE 5

| In lighter clot subgroup (90–126 mg): | Clot reduction % | Clot weight reduction |
|---|---|---|
| SK + USD (n = 13) | 78 ± 14% | 82 ± 12 mg |
| SK alone (n = 2) | 35 ± 4% | 55 ± 14 mg |

TABLE 6

| In heavier clot subgroup (228–357 mg): | Clot reduction % | Clot weight reduction |
|---|---|---|
| SK + USD (n = 13) | 71 ± 8% | 215 ± 34 mg |
| SK alone (n = 2) | 30 ± 5 | 90 ± 25 mg |

EXAMPLE VII

Utilizing the same experimental setup as in Example I, the effect of ultrasound mode on thrombolysis has been determined. With 250 µ/ml streptokinase, the one-hour old clots were exposed to continuous and pulsed ultrasound for 30 minutes. The effect of different ultrasound modes on thrombolysis is as follows:

Continuous mode: The average clot reduction was 78±18% (net reduction of the clot weight was 80±15 mg, n=8).

Pulsed mode: The average clot reduction was 78±8% (net reduction of the clot weight was 84± mg, n=5).

EXAMPLE VIII

The experimental setup as in Example I has been utilized to perform experiments sixteen rabbits for evaluating an apparatus of the present invention which utilizes external, transcutaneous ultrasound to remove arterial thrombi.

Figure 2:
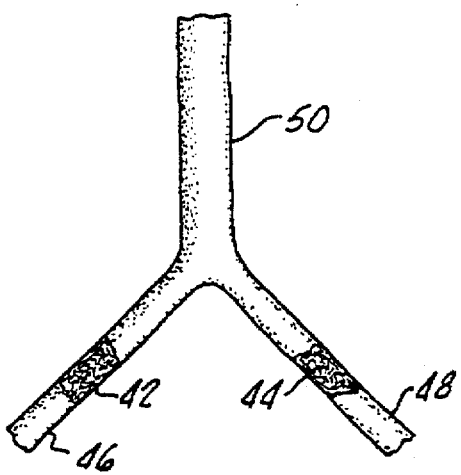
FIG. 2 is a representation of an aorta having bilateral thrombosis induced in iliofemoral arteries.

As illustrated in FIG. 2, arterial occlusions 42,44 were induced in bilateral iliofemoral arteries 46, 48 communicating with the aorta 50. The occlusions 42, 44 were formed by a combination of balloon abrasion followed by electrical induction of a thrombus by a guide wire (not shown). The bilateral iliofemoral thrombi 42, 44 were created after fifteen minutes of electrical energy to the iliofemoral arteries and the bilateral iliofemoral occlusions so formed were documented by X-ray angiography. FIG. 2 shows the contralateral artery 46 and the iliac artery 48.

After formation of the occlusions, the rabbits were given low doses of streptokinase, of about 25,000 units per kilogram of rabbit weight, so that both thrombolytic occlusions 46, 48 were exposed to streptokinase.

Thereafter, each rabbit was exposed to transcutaneous ultrasound of a frequency of 28 kHz, applied over the region of the iliac artery occlusion 44. Serial angiograms were performed after thrombus induction, after thrombosis occlusion and during and after ultrasound exposure.

Both iliofemoral arteries 46, 48 and soft tissues between the ultrasound transducer and the arteries were obtained for gross and microscopic pathological examination.

Figure 3:
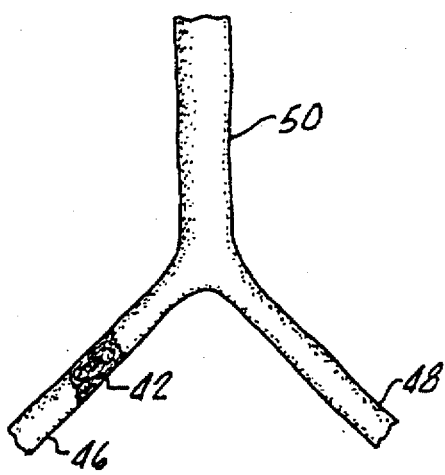
FIG. 3 is a representation similar to that shown in FIG. 2 after one of the thrombi in the iliofemoral arteries has been removed in accordance with the apparatus and method of the present invention.

In 9 out of 16 rabbits, the occluded iliac iliofemoral arteries 48 exposed externally to 28 kHz of ultrasound were shown by angiography to be recanalized, as represented by FIG. 3. However, in the control contralateral iliofemoral arteries 46, exposed to streptokinase alone, the arteries 46 remained occluded in 16 out of 16 rabbits. Similarly, microscopy revealed that the arteries exposed to ultrasound was patent, and that the contralateral arteries remained occluded. Thus, it has been concluded that transcutaneously applied ultrasound is effective for augmenting clot lysis where a given dose of streptokinase fails to work.

EXAMPLE IX

Experimental Setup

In an experiment similar to Example VII, thrombosis was induced in rabbits as hereinabove described and a 25,000 u/kg dose of streptokinase was administered, in order to study the effects of pulsed and continuous ultrasound on thrombi. Continuous ultrasound and pulsed wave ultrasound were utilized with the pulsed wave ultrasound having a duty cycle of about 30 milliseconds.

Utilizing X-ray confirmation, only one occlusion in the iliofemoral artery was radiated by ultrasound with the other occlusion in the other iliofemoral artery not being exposed to the ultrasound. After 37 minutes, at a power level of up to about 40 microamperes, the iliofemoral thrombosis exposed to the ultrasound was completely dissolved. In contrast, the unexposed iliofemoral artery remained totally occluded.

The same results were obtained through pulsed ultrasonic radiation except that a time of 40 minutes was required to totally remove the occlusion from the exposed artery, while the unexposed artery remained occluded.

EXAMPLE X

Utilizing the same experimental setup as in Example 1, the potential of microbubbles, to enhance high intensity, low frequency ultrasound clot dissolution was studied, with 2% Dodecafluoropentane (DFP), which makes a phase shift at body temperature from liquid to microbubbles, in combination with three minutes of ultrasound at different frequencies. Ultrasound frequencies tested were 105 kHz, 53.3 kHz, and 24.8 kHz.

Sixty four blood clots, one to four hours old, and weighing approximately 400–500 mg, were placed in a beaker of saline for three minutes. In half of the cases, saline alone was studied; in the other half of the study DFP was added to the saline solution. The frequencies of 24.8, 53.3, and 105.4 kHz were tested as well as no ultrasound, with and without the DFP. Specifically, the test included eight controls and eight at each of the three ultrasound frequencies both with and without the echo contrast agent, DFP. The results are shown in the following Tables.

Results

For the control clots in saline alone, there was 45±25 mg of reduction in clot weight. This was similar to the control clots with the DFP added and no ultrasound (33±26 mg reduction of clot weight.)

It can be seen by comparison of Tables 15 and 16 which summarizes the results, the addition of the echo contrast agent, DFP, significantly enhances ultrasound clot dissolution in vitro. With the application of ultrasound at 105 kHz there was 19% of clot dissolved compared to 29% with the addition of the DFP. At a frequency of 53.3 kHz there was 22% dissolution compared to 79% with the DFP. At the lowest frequency tested of 24.8 kHz, there was 72% of clot dissolved compared to 98% in the group receiving DFP. Thus, at frequencies of 53.3 and 24.8 kHz, there is a considerable increase in the amount of clot dissolution in a three minute period. Such an augmentation in clot dissolution may have significant potential for enhancing the efficacy of in vivo ultrasound thrombus dissolution.

TABLE 7

No USD, saline alone

|   | Pre (mg) | Post (mg) | Des. clot (mg) | % reduction | Temp. | Clot age (min.) |
|---|---|---|---|---|---|---|
| 1 | 451 | 392 | 59 | 13.1 | 38 | 85 |
| 2 | 439 | 340 | 99 | 22.6 | 36 | 105 |
| 3 | 466 | 425 | 41 | 8.8 | 36 | 130 |
| 4 | 506 | 463 | 43 | 8.5 | 39 | 166 |
| 5 | 477 | 455 | 22 | 4.6 | 37 | 122 |
| 6 | 499 | 460 | 39 | 7.8 | 37 | 135 |
| 7 | 444 | 412 | 32 | 7.2 | 37 | 140 |
| 8 | 492 | 465 | 27 | 5.5 | 39 | 152 |
| mean | 471.8 | 426.5 | 45.3 | 9.8 | 37.4 | 129.4 |
| SD | 25.8 | 44.1 | 24.5 | 5.8 | 1.2 | 25.7 |

TABLE 8

No USD, Echogen 1 ml/100 ml saline

|   | Pre (mg) | Post (mg) | Des. clot (mg) | % reduction | Temp. | Clot age (min.) |
|---|---|---|---|---|---|---|
| 1 | 489 | 460 | 29 | 5.9 | 36 | 120 |
| 2 | 500 | 485 | 15 | 3.0 | 36 | 120 |
| 3 | 464 | 443 | 21 | 4.5 | 36 | 130 |
| 4 | 508 | 484 | 24 | 4.7 | 39 | 166 |
| 5 | 490 | 460 | 30 | 6.1 | 37 | 122 |
| 6 | 476 | 459 | 17 | 3.6 | 37 | 135 |
| 7 | 470 | 440 | 30 | 6.4 | 37 | 140 |

TABLE 8-continued

No USD, Echogen 1 ml/100 ml saline

|   | Pre (mg) | Post (mg) | Des. clot (mg) | % reduction | Temp. | Clot age (min.) |
|---|---|---|---|---|---|---|
| 8 | 510 | 416 | 94 | 18.4 | 38 | 152 |
| mean | 488.4 | 455.9 | 32.5 | 6.6 | 37.0 | 135.6 |
| SD | 17.2 | 23.0 | 25.5 | 4.9 | 1.1 | 16.5 |

TABLE 9

3 min USD (24.8 kHz) alone

|   | Pre (mg) | Post (mg) | Des. clot (mg) | % reduction | Temp. | Clot age (min.) |
|---|---|---|---|---|---|---|
| 1 | 460 | 27 | 433 | 94.1 | 39 | 145 |
| 2 | 460 | 89 | 371 | 80.7 | 39 | 145 |
| 3 | 450 | 148 | 302 | 67.1 | 39 | 150 |
| 4 | 480 | 104 | 376 | 78.3 | 39 | 150 |
| 5 | 426 | 35 | 391 | 91.8 | 40 | 162 |
| 6 | 534 | 263 | 271 | 50.7 | 40 | 162 |
| 7 | 543 | 280 | 263 | 48.4 | 40 | 170 |
| 8 | 515 | 199 | 316 | 61.4 | 40 | 170 |
| mean | 483.5 | 143.1 | 340.4 | 71.6 | 39.5 | 156.8 |
| SD | 42.5 | 97.0 | 61.2 | 17.5 | 0.5 | 10.5 |

TABLE 10

3 min USD (24.8 kHz) with Echogen (1 ml/100 ml saline)

|   | Pre (mg) | Post (mg) | Des. clot (mg) | % reduction | Temp. | Clot age (min.) |
|---|---|---|---|---|---|---|
| 1 | 485 | 0 | 485 | 100.0 | 39 | 156 |
| 2 | 512 | 0 | 512 | 100.0 | 39 | 156 |
| 3 | 516 | 54 | 462 | 89.5 | 40 | 163 |
| 4 | 527 | 0 | 527 | 100.0 | 40 | 163 |
| 5 | 473 | 5 | 468 | 98.9 | 39 | 176 |
| 6 | 450 | 9 | 441 | 98.0 | 39 | 176 |
| 7 | 451 | 1 | 450 | 99.8 | 40 | 182 |
| 8 | 502 | 3 | 499 | 99.4 | 40 | 182 |
| mean | 489.5 | 9.0 | 480.5 | 98.2 | 39.5 | 169.3 |
| SD | 29.5 | 18.5 | 30.5 | 3.6 | 0.5 | 11.0 |

TABLE 11

3 min USD (53.3 kHz) alone

|   | Pre (mg) | Post (mg) | Des. clot (mg) | % reduction | Temp. | Clot age (min.) |
|---|---|---|---|---|---|---|
| 1 | 442 | 299 | 143 | 32.4 | 38 | 105 |
| 2 | 537 | 388 | 149 | 27.7 | 38 | 105 |
| 3 | 490 | 360 | 130 | 26.5 | 37 | 120 |
| 4 | 456 | 346 | 110 | 24.1 | 37 | 120 |
| 5 | 440 | 370 | 70 | 15.9 | 39 | 125 |
| 6 | 437 | 362 | 75 | 17.2 | 39 | 125 |
| 7 | 530 | 437 | 93 | 17.5 | 40 | 132 |
| 8 | 428 | 350 | 78 | 18.2 | 40 | 132 |
| mean | 470.0 | 364.0 | 106.0 | 22.4 | 38.5 | 120.5 |
| SD | 43.5 | 39.1 | 31.7 | 6.1 | 1.2 | 10.6 |

TABLE 12

3 min USD (53.3 kHz) with Echogen (1 ml/100 ml saline)

|   | Pre (mg) | Post (mg) | Des. clot (mg) | % reduction | Temp. | Clot age (min.) |
|---|---|---|---|---|---|---|
| 1 | 467 | 63 | 404 | 86.5 | 39 | 136 |
| 2 | 422 | 58 | 364 | 86.3 | 39 | 136 |
| 3 | 443 | 33 | 410 | 92.6 | 39 | 243 |
| 4 | 467 | 158 | 309 | 66.2 | 39 | 243 |
| 5 | 414 | 150 | 264 | 63.8 | 39 | 138 |
| 6 | 490 | 50 | 440 | 89.8 | 39 | 138 |
| 7 | 517 | 226 | 291 | 56.3 | 39 | 155 |
| 8 | 490 | 35 | 455 | 92.9 | 39 | 155 |
| mean | 463.8 | 96.6 | 367.1 | 79.3 | 39.0 | 168.0 |
| SD | 35.6 | 71.7 | 71.8 | 14.7 | 0.0 | 47.0 |

TABLE 13

3 min USD (105.4 kHz) alone

|   | Pre (mg) | Post (mg) | Des. clot (mg) | % reduction | Temp. | Clot age (min.) |
|---|---|---|---|---|---|---|
| 1 | 510 | 431 | 79 | 15.5 | 36 | 70 |
| 2 | 508 | 330 | 178 | 35.0 | 36 | 70 |
| 3 | 464 | 370 | 94 | 20.3 | 38 | 78 |
| 4 | 552 | 436 | 116 | 21.0 | 38 | 78 |
| 5 | 490 | 381 | 109 | 22.2 | 39 | 81 |
| 6 | 516 | 463 | 53 | 10.3 | 39 | 81 |
| 7 | 420 | 383 | 37 | 8.8 | 39 | 90 |
| 8 | 431 | 335 | 96 | 22.3 | 39 | 90 |
| mean | 486.4 | 391.1 | 95.3 | 19.4 | 38.0 | 79.8 |
| SD | 45.0 | 48.2 | 42.9 | 8.2 | 1.3 | 7.6 |

TABLE 14

3 min USD (105.4 kHz) with Echogen (1 ml/100 ml saline)

|   | Pre (mg) | Post (mg) | Des. clot (mg) | % reduction | Temp. | Clot age (min.) |
|---|---|---|---|---|---|---|
| 1 | 490 | 300 | 190 | 38.8 | 39 | 85 |
| 2 | 475 | 293 | 182 | 38.3 | 39 | 85 |
| 3 | 450 | 280 | 170 | 37.8 | 37 | 95 |
| 4 | 475 | 313 | 162 | 34.1 | 37 | 95 |
| 5 | 459 | 339 | 120 | 26.1 | 39 | 96 |
| 6 | 512 | 399 | 113 | 22.1 | 39 | 96 |
| 7 | 508 | 426 | 82 | 16.1 | 39 | 115 |
| 8 | 540 | 452 | 88 | 16.3 | 39 | 115 |
| mean | 488.6 | 350.3 | 238.4 | 28.7 | 38.5 | 97.8 |
| SD | 30.0 | 66.2 | 42.8 | 9.8 | 0.9 | 11.6 |

TABLE 15

| 3 minutes ultrasound alone (kHz) | Clot weight reduction (mg) | Clot weight reduction (%) |
|---|---|---|
| 105 | 95 ± 32 | 19 |
| 53.3 | 106 ± 32 | 22 |
| 24.8 | 340 ± 61 | 72 |

TABLE 16

| 3 minutes ultrasound (kHz) with Dodecafluropentane (1 ml/100 ml saline) | Clot weight reduction (mg) | Clot weight reduction (%) |
| --- | --- | --- |
| 105 | 138 ± 43 | 29 |
| 53.3 | 367 ± 72 | 79 |
| 24.8 | 481 ± 31 | 98 |

Although there has been hereinabove described a specific arrangement of ultrasonic apparatus and a method for thrombi dissolution in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for removing a thrombosis, said method comprising the steps of:
   (a) radiating a thrombosis, disposed in a vessel within a body, with ultrasound in order to effect removal of the thrombosis by dissolution thereof, said ultrasound being introduced at a frequency of less than about 100 kHz; and
   (b) introducing a selected dose of an echo contrast agent proximate the thrombosis in order to enhance the effectiveness of the ultrasound in removing the thrombosis by dissolution thereof.

2. The method according to claim 1 wherein the ultrasound is applied transcutaneously.

3. The method according to claim 1 wherein the ultrasound is applied intravascularly.

4. The method according to claim 1 wherein the ultrasound is introduced at a frequency of between about 24 kHz and about 53 kHz.

5. The method according to claim 1 wherein the ultrasound is introduced at a frequency of between about 24 kHz and about 53 kHz.

6. The method according to claim 1 wherein the echo contrast agent is comprised of a microbubble medium.

7. The method according to claim 6 wherein the microbubble medium is comprised of a medium selected from the group consisting of free gas bubbles, stabilized gas bubbles, colloidal suspensions, emulsions, and aqueous solutions.

8. The method according to claim 7 wherein the microbubble medium is a colloidal suspension comprising dodecafluropentane.

9. The method according to claim 7 wherein the microbubble medium is an aqueous solution comprised of sonicated albumin.

10. A method for enhancing thrombolytic action of a thrombolytic agent, said method comprising the steps of:
    (a) radiating a thrombosis, disposed in a vessel within a body, with ultrasound in order to effect removal of the thrombosis, said ultrasound having a frequency of less than about 100 kHz;
    (b) introducing a selected dose of a thrombolytic agent proximate the thrombosis; and
    (c) introducing a selected dose of an echo contrast agent proximate the thrombosis in order to enhance the effectiveness of both the ultrasound and the thrombolytic agent in removing the thrombosis.

11. The method according to claim 10 wherein the ultrasound is applied transcutaneously.

12. The method according to claim 10 wherein ultrasound is applied intravascularly.

13. The method according to claim 10 wherein streptokinase is introduced as the thrombolytic agent.

14. The method according to claim 10 wherein the echo contrast agent is comprised of a microbubble medium.

15. The method according to claim 14 wherein the microbubble medium is comprised of a medium selected from the group consisting of free gas bubbles, stabilized gas bubbles, colloidal suspensions, emulsions, and aqueous solutions.

16. The method according to claim 15 wherein the microbubble medium is a colloidal suspension comprising dodecafluropentane.

17. The method according to claim 15 wherein the microbubble medium is an aqueous solution comprising sonicated albumin.

18. Apparatus for removal of a cardiovascular blockage, said apparatus comprising, in combination:
    ultrasonic means for radiating a cardiovascular blockage with ultrasound, having a frequency of less than about 100 kHz; and
    means for introducing a selected dose of an echo contrast agent proximate the cardiovascular blockage in order to enhance the effect of the ultrasound in removing the cardiovascular blockage.

19. The apparatus of claim 18 wherein the echo contrast agent is a microbubble medium selected from the group consisting of free gas bubbles, stabilized gas bubbles, colloidal suspensions, emulsions, and aqueous solutions.

* * * * *